United States Patent
Onodera et al.

(10) Patent No.: US 7,891,976 B2
(45) Date of Patent: Feb. 22, 2011

(54) BRUXISM EVALUATION SHEET

(75) Inventors: Kanji Onodera, Tokyo (JP); Sadao Sato, Yokosuka (JP)

(73) Assignees: Rocky Mountain Morita Corp., Tokyo (JP); Kanagawa Dental College, Kanagawa (JP)

( * ) Notice: Subject to any disclaimer, the term of this patent is extended or adjusted under 35 U.S.C. 154(b) by 605 days.

(21) Appl. No.: 11/720,581

(22) PCT Filed: Nov. 29, 2005

(86) PCT No.: PCT/JP2005/021843

§ 371 (c)(1),
(2), (4) Date: Dec. 5, 2007

(87) PCT Pub. No.: WO2006/059587

PCT Pub. Date: Jun. 8, 2006

(65) Prior Publication Data

US 2008/0211123 A1 Sep. 4, 2008

(30) Foreign Application Priority Data

Dec. 3, 2004 (JP) .............................. 2004-350654

(51) Int. Cl.
*A61C 19/04* (2006.01)
*A61C 19/05* (2006.01)
(52) U.S. Cl. ............................ 433/68; 433/69; 433/70; 433/71; 433/54
(58) Field of Classification Search ........................ None
See application file for complete search history.

(56) References Cited

U.S. PATENT DOCUMENTS 2,633,637 A * 4/1953 Lucia ........................... 433/70
3,694,237 A * 9/1972 Piotrowski ................ 106/31.42
4,198,243 A * 4/1980 Tanaka ..................... 106/31.03

(Continued)

FOREIGN PATENT DOCUMENTS

JP 58011552 A 1/1983

(Continued)

OTHER PUBLICATIONS

XP002477478, Database WPI Week 198309 Thomson Scientific, London, GB, 1983-21276K.

(Continued)

*Primary Examiner*—Edmund H. Lee
(74) *Attorney, Agent, or Firm*—Ping Wang; Andrews Kurth, LLP

(57) ABSTRACT

The purpose of the present invention is to develop an apparatus that can examine the occlusal contact patterns during the sleep bruxism, which can not be evaluated by the observation of the interior of oral cavity or by means of the articulator, in order to establish a convenient evaluation means for employing bruxism in daily and clinical diagnosis. The present invention relates to a bruxism evaluation sheet having a layer comprising an aqueous solution composition of an organic solvent comprising a dye and a thermosetting resin on a base sheet made of a thermoplastic resin, and a method for producing a convenient bruxism evaluation apparatus comprising heating the bruxism evaluation sheet, vacuum pressing it onto a model and then molding, and the like.

15 Claims, 7 Drawing Sheets
(5 of 7 Drawing Sheet(s) Filed in Color)

U.S. PATENT DOCUMENTS

| | | | |
|---|---|---|---|
| 5,624,484 | A | 4/1997 | Takahashi et al. |
| 6,244,864 | B1 * | 6/2001 | Fujiwara et al. ............... 433/71 |
| 2007/0275346 | A1 * | 11/2007 | Mannschedel et al. ........ 433/70 |
| 2008/0038687 | A1 * | 2/2008 | Mannschedel et al. ........ 433/70 |

FOREIGN PATENT DOCUMENTS

| | | | |
|---|---|---|---|
| JP | 63-119753 | A | 5/1988 |
| JP | 8-81611 | A | 3/1996 |
| JP | 8-291042 | A | 11/1996 |
| JP | 2001-181139 | A | 7/2001 |
| JP | 2005-97277 | A | 4/2005 |
| JP | 2005-314697 | A | 11/2005 |

OTHER PUBLICATIONS

Supplementary European Search Report.

International Search Report, International Patent Application No. PCT/JP2005/021843, filed Nov. 29, 2005.

McNeill, C., DDS (ed.), "Temporomandibular Disorders: Guidelines for Classification, Assessment, and Management," Chicago: The American Academy of Orofacial Pain, Quintessence Books, pp. 11-18 (1993).

Trenouth, M.J., "The relationship between bruxism and temporomandibular joint dysfunction as shown by computer analysis of nocturnal tooth contact patterns," J. Oral. Rehabil., vol. 6, pp. 81-87 (1979).

Coleman, T.A., DDS, et al., "Cervical dentin hypersensitivity. Part II: Associations with abfractive lesions," Quintessence Int., vol. 31, No. 7, pp. 466-473 (2000).

Slavicek, R. (ed.), "The function of stress management. In: The Masticatory Organ-Function and Dysfunction," Klosterneuburg, Gamma Medizinisch-wissenschaftliche Fortdungs-AG, pp. 281-291 (2002).

Sato, S., et al., "Bruxism as a Stress Management Function of the Masticatory Organ," Bull. Kanagawa Dent. Coll., vol. 29, No. 2, September, pp. 101-110 (2001).

Sato, S, et al., "The Masticatory Organ, Brain Function, Stress-release, and a Proposal to Add a New Category to the Taxonomy of the Healing Arts: Occlusion Medicine," Bull. Kanagawa Dent. Coll., vol. 30, No. 2, September, pp. 117-126 (2002).

Sjöholm, T., et al., "Masseter muscle activity in diagnosed sleep bruxists compared with non-symptomatic controls," J. Sleep Res., vol. 4, pp. 48-55 (1995).

Lavigne, G.J., et al., "Bruxism," Principles and Practice of Sleep Medicine, 3rd Edition, Kryger, M.H., Roth, T., Dement, W.C., editors, Philadelphia: Saunders, W.B., pp. 773-785 (2000).

* cited by examiner

BRUXISM EVALUATION SHEET

FIELD

This invention relates to a bruxism evaluation sheet that is used in an apparatus for conveniently evaluating tooth contact patterns during sleep bruxism, and to an aqueous dye composition applied to the sheet.

BACKGROUND

Sleep bruxism is generally defined as a diurnal or nocturnal parafunctional activity involving: clenching, grinding and gnashing of the teeth. It has been considered that such sleep bruxism is a causatic factor for tremendous problems in odontology (McNeill, C., DDS (ed.), "Temporomandibular Disorders: Guidelines for Classification, Assessment, and Management," Chicago: The American Academy of Orofacial Pain, Quintessence Books, pp. 11-18[1993]). Excessive dental attrition can never occur any more in the dietary life of modern people, because tooth contacts of the maxillary and mandibular casts will hardly happen during masticatory (chewing) movement of foods taken by the modern people. On the other hand, it is reported that the sleep bruxism may last for from 20 to 40 minutes, in some cases for 2 hours, during a one-night sleep (Trenouth, M. J., "The relationship between bruxism and temporomandibular joint dysfunction as shown by computer analysis of nocturnal tooth contact patterns," J. Oral Rehabil., Vol. 6, pp. 81-87[1979]).

It is said that the maximum occlusal force generated by masticatory muscles at the time of the sleep bruxism is significantly greater than the force required to fracture teeth. While neuromuscular mechanism is considered to consciously reduce muscular strength against the load suddenly applied against the teeth in order to prevent disorder in a living body, it does not have a function to unconsciously reduce the force applied to enamel or dentinal matrix. Especially, the forces caused by the sleep bruxism may be considered to be out of control by such neuromuscular mechanism.

It is considered that such sleep bruxism has caused a risk to generate many dental disorders such as tooth abfractions, tooth migration, hyperesthesia, wedge-shaped defect, periodontoclasia, dysfunction of temporomandibular joints, and hypertonic masticatory muscles (Coleman, T. A., DDS, et al., "Cervical dentin hypersensitivity. Part II: Associations with abfractive lesions," Quintessence Int., Vol. 31, No. 7, pp. 466-473[2000]).

Conventional dental occlusion treatments have been studied mainly on masticatory function for a long time, and the purpose of clinical occlusion treatment has been limited only to recovery of masticatory function. In such normal masticatory function by humans, the load applied to teeth, periodontal tissue, temporomandibular joints and the like is not so large that biomechanical consideration has not been seriously taken in occlusal construction. However, since the bruxism function is a very strong masticatory muscle activity, the load applied to teeth, periodontal tissue, and temporomandibular joints may reach a maximum level. Accordingly, it has been recently proposed that the bruxism takes a very important role of a masticatory organ for releasing emotional stress (Slavicek, R. (ed.), "The function of stress management. In: The Masticatory Organ-Function and Dysfunction," Klostemeuburg, Gamma Medizinish-wissenschaftliche Fortdungs-AG, pp. 281-291[2002]; Sato, S., et al., "Bruxism as a Stress Management Function of the Masticatory Organ," Bull. Kanagawa Dent. Coll., Vol. 29, No. 2, September, pp. 101-110[2001]), and it has also been suggested that the conventional dental occlusion treatment system should be fundamentally changed (Sato, S., et al., "The Masticatory Organ, Brain Function, Stress-release, and a Proposal to Add a New Category to the Taxonomy of the Healing Arts: Occlusion Medicine," Bull. Kanagawa Dent. Coll., Vol. 30, No. 2, September, pp. 117-126[2002]). As just described, although the bruxism has now been recognized as a very important issue in clinical dentistry, little approach has been actually made for it.

Thus, up to now, the bruxism has been studied by means of huge facilities such as a sleeping laboratory, polysomnography, electromyography and the like (Sjöholm, T., et al., "Masseter muscle activity in diagnosed sleep bruxists compared with non-symptomatic controls," J. Sleep Res., Vol. 4, pp. 48-55[1995]; Lavigne, G. J., et al., "Bruxism," Principles and Practice of Sleep Medicine, 3rd Edition, Kryger M. H., Roth, T., Dement, W. C., editors, Philadelphia: Saunders, W. B., pp. 773-785[2000]). Although these facilities seem to be important for an academic purpose, they are not suited for an application to the daily and clinical diagnosis of a patient. It has been pointed out that many problems in clinical sites such as tooth abfractions, tooth migration, hyperesthesia, wedge-shaped defect, periodontoclasia, dysfunction of temporomandibular joints, and hypertonic masticatory muscles as well as destruction of prosthetic apparatus after treatment and occlusal disruption are attributed to the sleep bruxism and abnormal occlusal contacts during the sleep bruxism. However, there is no method to adequately measure them.

Occlusal construction will finally be required in clinical dentistry. There has been reported very little actual countermeasure against stress bruxism in the course of said construction. The final purpose of dental medicine is considered to contribute to maintenance of good health of an entire body by taking harsh physical environments into account and completing occlusion in response to them. It has to be admitted that progress is very slow with respect to diagnosis of the bruxism.

DISCLOSURE OF THE INVENTION

Problem to be Solved

As muscle activities during the sleep bruxism that occurs unconsciously will be maximized when molars are contacted, it is necessary to provide occlusion without any contact of the molars in order to decrease the muscle activities during the sleep bruxism. Up to now, however, although the interior of the oral cavity is directly observed and the contact conditions on an articulator are observed, there has been no proper evaluation means for the contacts of the molars during the sleep bruxism. Accordingly, it is desired to develop a convenient or simple evaluation means that can be employed in the daily and clinical diagnosis of an individual patient.

The purpose of the invention is therefore to solve the above problems, and to develop an apparatus that can be used to examine the occlusal contact patterns during the sleep bruxism, which cannot be evaluated by the observation of the interior of oral cavity or by means of the articulator, in order to establish a convenient evaluation means for employing bruxism in daily and clinical diagnosis.

Means for Solving the Problems

Thus, the present invention, as its first aspect, is related to an aqueous solution composition of an organic solvent comprising a dye and a thermosetting resin. It also relates to a bruxism evaluation sheet having a layer comprising the aqueous solution composition on a base sheet made of a thermoplastic resin. It further relates to a method for producing a convenient bruxism evaluation apparatus comprising heating the bruxism evaluation sheet, vacuum pressing it onto a model and then molding.

Advantages of the Invention

By mounting the convenient bruxism evaluation apparatus according to the present invention with a subject, it will be possible to visually and clearly observe the contact patterns by the bruxism during nocturnal sleep without any uncomfortable feeling when it is mounted. Thus, the present invention makes it possible to observe the occlusal contact, which cannot be evaluated by the observation of the interior of the oral cavity or by means of an articulator, and to provide the bruxism evaluation apparatus that can be applied in daily and clinical diagnosis of each patient.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
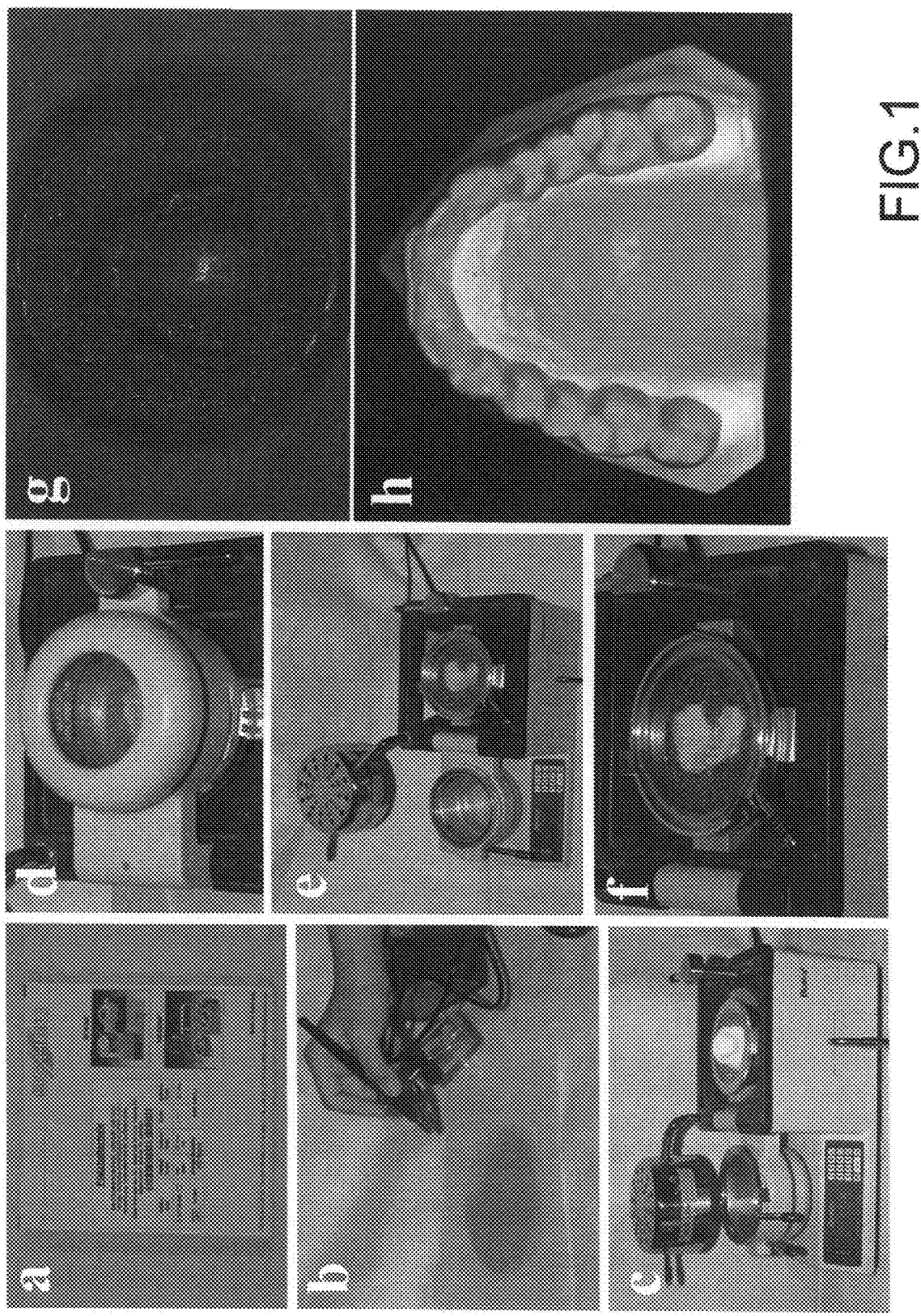
FIGS. 1(a)-(h) are photographs showing production steps of the convenient bruxism evaluation apparatus according to the present invention.

Best Mode for Carrying Out the Invention

The following description will not limit or restrict the scope of the present invention. It is considered that in the aqueous solution composition of the first aspect of the present invention is directed to the thermosetting resin having a function to fix the dye on the surface of the base sheet with thermosetting. Such thermosetting resin, which is known to one of those skilled in the art, includes such as unsaturated polyester resin, phenol resin, urea resin, melamine resin, epoxy resin and polyurethane resin, which are commercially available as molded articles such as tableware, paint and adhesive. Natural resin is preferable in view of safety.

Shellac may be listed as a representative example of the above natural resin. Shellac is a polyester resin-like material that is secreted by *Lacciferlacca* korr, an insect belonging to a scale family, which parasitizes woods of pulse and moraceous families. It comprises 65-80% of resin in the form of lactide with aleuritic acid and shellolic acid, wax in the form of an ester between ceryl alcohol and myricyl alcohol and myricinic acid and cerotic acid, 0.6-3% of aqueous dye, 2-6% of proteins, sugars and soluble salts, 1-4% of water, and 7-18% of water- and alcohol-insoluble materials. It is used as a base material for chewing gum, a brightening agent of membrane of citrus, and a polishing agent for confectionery and coffee products.

Shellac is insoluble in water, but soluble in alcohol such as ethanol at a room temperature. After thermosetting, it will form a membrane showing strong and excellent resistance to oil, heat and abrasion, adhesiveness, endurance and glazing.

Usually, shellac is purified by filtration in a molten or solution state. It has many types such as a wax-containing type, dewaxed type, one bleached or decolored with alkali aqueous solution and the like. Any type of the commercially available products may be used as "shellac" in the present invention.

When the convenient bruxism evaluation apparatus is mounted with the subject, grinding of teeth during the sleep bruxism will grind off the resin comprising the dye, which has been thermoset on the bruxism evaluation sheet, to leave the ground part clouded, so that it will be possible to visually and clearly observe the contact patterns.

Accordingly, there is no limitation on the kind and origin of the dye as long as it has such function. Considering safety, however, a food coloring agent is preferable as the dye, since the convenient bruxism evaluation apparatus is mounted into the oral cavity. Any food coloring agent known to those skilled in the art may be used. There is no limitation with respect to the color of the coloring agent. For example, Acid Red 51 (Food Red No. 3, Erythrosine B, Tetraiodofluorescein sodium salt) (Morimura, Tokyo) may be listed. Further, the food coloring agent includes carotenoid pigment, flavonoid pigment, porphyrin pigment, curcuma and various synthetic pigments.

The organic solvent used in the present aqueous solution composition preferably dissolves the dye and the thermosetting resin, and may be optionally selected depending on their kinds. Usually, alcohol such as ethanol is suitable. The ratio between the organic solvent and water may be optionally selected as well, being usually in a range of 90:10~95.5~0.5 (the organic solvent:water).

There is no limitation on the content of the dye and thermosetting resin comprised in the aqueous solution, as long as the tooth contact conditions may be visually and clearly observed. For example, the dye is comprised in an amount of usually 1~3% by weight, preferably 2~2.5% by weight, and the thermosetting resin is comprised in an amount of usually 20~40% by weight, preferably 25~30% by weight.

The present aqueous solution composition of the organic solvent may optionally comprise any other ingredients known to those skilled in the art, such as fragrance, fluorine, medicine for cold, cough suppressant and traditional Chinese medicine as long as they would not harm the particular effects by the composition.

The bruxism evaluation sheet of the second aspect of the present invention has a layer comprising the aqueous solution composition on a base sheet made of a thermoplastic resin. The thermoplastic resin includes any material known to those skilled in the art such as polyvinyl chloride, polypropylene and polyethylene. The layer comprising the aqueous solution composition of the organic solvent may be easily prepared by, for example, painting the composition directly on the base sheet with a brush, or spraying it with an air sprayer. In order to obtain the desired advantages of the present invention, it is preferable to make the thickness of the layer as uniform as possible, the thickness not being particularly limited but usually in a range of 30-100 μm.

The third aspect of the present invention is to provide a method for producing a convenient bruxism evaluation apparatus comprising heating the bruxism evaluation sheet, vacuum pressing it onto a model such as a plaster cast that has been formed by copying the denture mold of a subject, and then molding, for example, by trimming it along the gingival margin. During the heating process, the thermosetting resin comprised in the aqueous solution composition applied on the base sheet will harden so that the dye can be fixed on the base sheet.

The thickness of the base sheet is preferably as thin as possible so that the base sheet will not interfere with occlusal or mandibular movement of the subject and uncomfortable feeling can be reduced as much as possible when it is mounted. On the other hand, as the bruxism evaluation sheet is vacuum pressed onto the denture mold of the subject, the sheet has such thickness as required for the vacuum-pressing. Accordingly, the thickness of the thermoplastic base sheet is usually in a range of 0.03-0.2 mm, preferably of 0.05-0.1 mm.

The heating of the bruxism evaluation sheet may be done by means of an appropriate apparatus known to those skilled in the art. Heating conditions such as temperature and time may be optionally determined by those skilled in the art depending on the kind and thickness of the sheet, and the kinds of the dye and thermosetting resin comprised in the aqueous solution composition of the organic solvent, being usually at 220° C. for about 15 seconds.

EXAMPLES

The present invention will be explained in more detail with the following examples. The scope of the present invention will not be restricted in any way by the examples.

The aqueous solution composition of the present invention was prepared by mixing ethanol aqueous solution (ethanol:water=99.5:0.5), shellac ("Japan shellac transparent, dry and white shellac", manufactured by Japan Shellac Industries Ltd.: Product Code: LAC-BDS00) (25% by weight) and the dye (Acid Red 51 (Food Red No. 3), Erythrosine B, Tetraiodofluorescein sodium salt, manufactured by Morimura, Tokyo) (2.5% by weight). The resulting aqueous solution composition was then applied on a polyvinylchloride sheet (0.1 mm thickness: Scheu-Dental, Germany: FIG. 1a) with an air sprayer (FIG. 1b) to obtain a bruxism evaluation sheet according to the present invention. The resulting sheet was heated at 220° C. for 15 seconds by Bioster (Scheu-Dental, Germany), and pressed under pressure on a plaster cast (FIG. 1c-g). After cooling, it was trimmed along with gingival margin (FIG. 1h), and molded to give a convenient bruxism evaluation apparatus (called "BruxChecker").

Test Example 1

Figure 2:
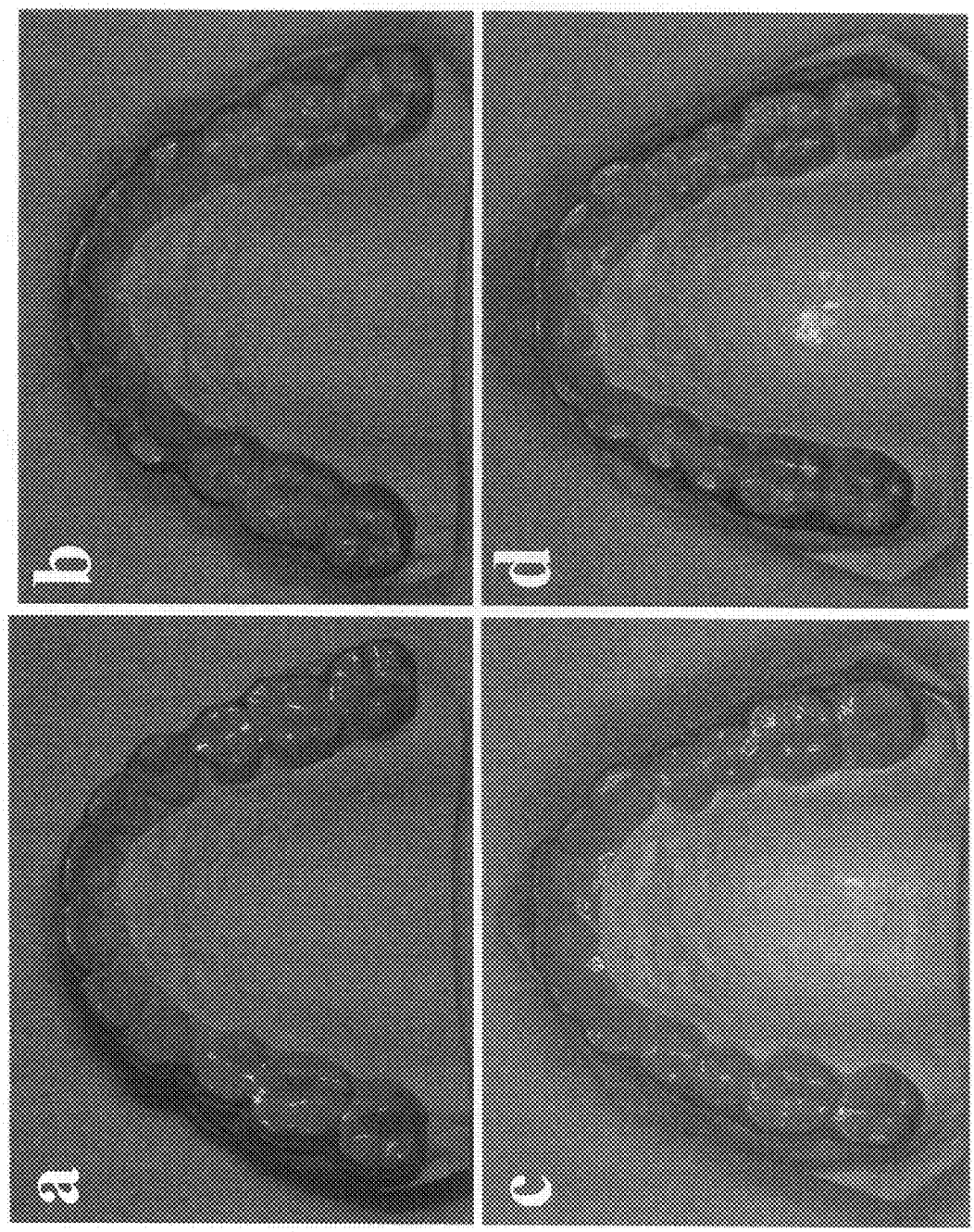
FIGS. 2(a)-(d) are photographs showing the tooth contact patterns during sleep bruxism, which were obtained by mounting the convenient bruxism evaluation apparatus with subjects. The photograph (a) shows an unmounted evaluation sheet (control), the photographs (b)-(d) show the contact patterns obtained by three subjects, respectively.

Three subjects wore the convenient bruxism evaluation apparatus during sleep (about 8 hours) to evaluate the tooth contact patterns. As a result, the dye in the occlusal contact areas was ground off during the sleep bruxism, and said areas were clearly identified as white spots (FIG. 2).

Figure 3:
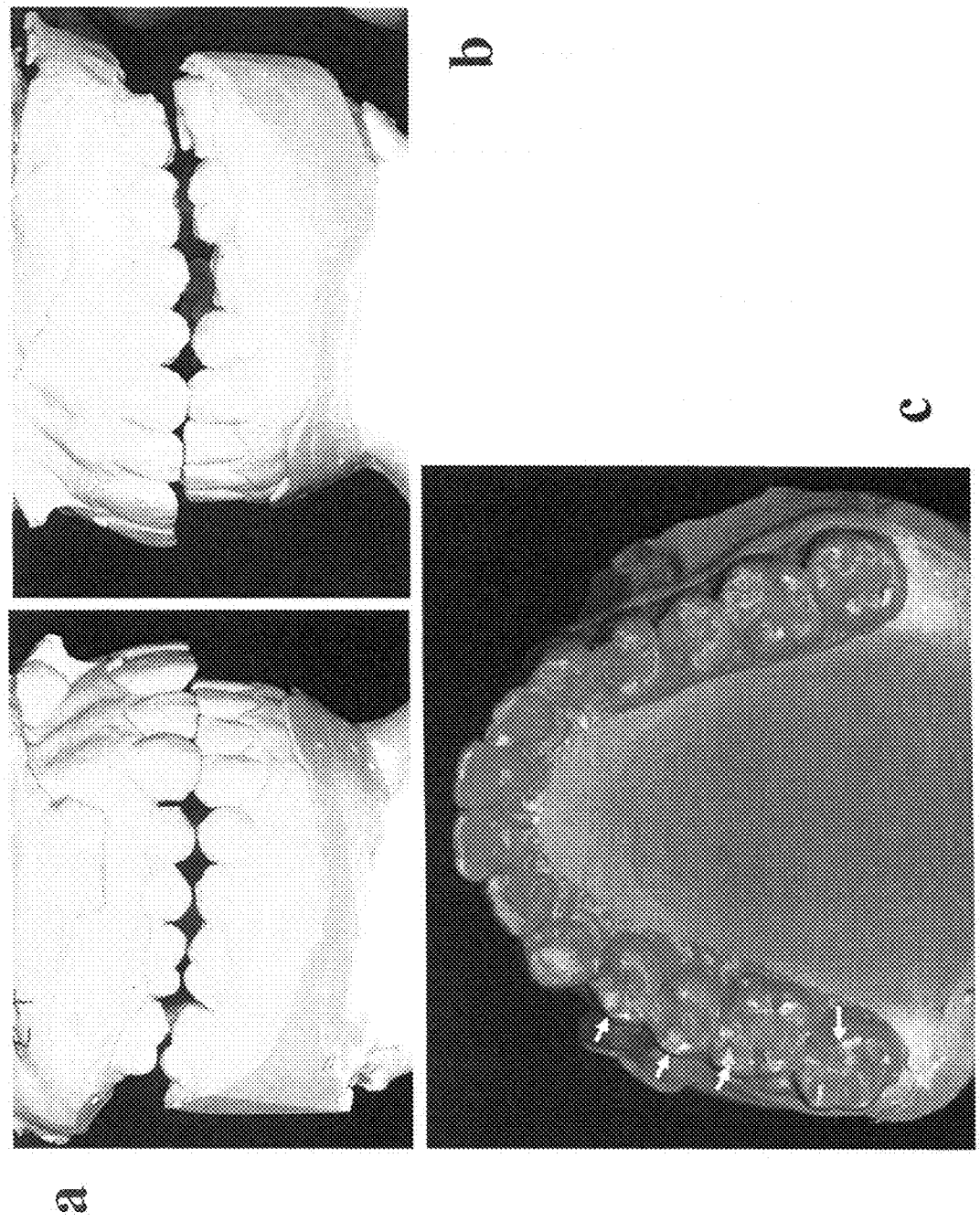
FIGS. 3(a)-(c) are photographs showing that the tooth contact patterns can be recognized by the bruxism evaluation apparatus (indicated with a white arrow) even in the case where the molars contact was not recognized by grinding of mandibular cast.

Simultaneously, occlusal casts of the subjects were mounted in a SAM 2 articulator by means of face bow transfer, and tooth grinding patterns in the articulator were examined. As a result, there were found distinctive differences between the tooth contact patterns by latero-retrusive movement of the mandible on the plaster occlusal cast attached to the articulator and those on the bruxism evaluation apparatus. Thus, the tooth contact patterns examined by the bruxism evaluation apparatus during sleep revealed many strong contacts in the molar areas due to latero-retrusive movement of the mandible even in the cases where any molar contact was not recognized in the articulator (FIG. 3).

Test Example 2

The test was performed for 50 subjects in total composed of 36 normal subjects and 14 subjects suffering from temporomandibular joint (TMJ) symptoms such as jointnoise, limitation of mouth opening and pain. None of the subjects has a defect from anterior to molar teeth, serious malocclusion, and any experience of large-scale prosthetic treatment.

These subjects wore the convenient bruxism evaluation apparatus (BruxChecker) during nocturnal sleep as in Test Example 2 to obtain the grinding patterns. Simultaneously, the maxillary and mandibular images and occlusion image of the subjects were taken. They were mounted in the articulator by means of face bow transfer to make a cast attached to the articulator, and tooth grinding patterns in the articulator were examined.

The grinding patterns obtained in the attached cast and those obtained actually during sleep were compared. As a result, there were found distinctive differences between the tooth contact patterns by latero-retrusive movement of the mandible on the plaster occlusal cast attached to the articulator and those on the bruxism evaluation apparatus. The grinding areas that could be visually identified were classified with the cast and BruxChecker. The TMJ-symptom group showed the tendency that many grinding patterns were observed in the molar area both in laterotrusion side and mediotrusion side. The contacts on mediotrusion side were observed by BruxChecker in both groups, which could not be recognized in the attached cast. Thus, the tooth contact patterns examined by the bruxism evaluation apparatus during sleep revealed many strong contacts in the molar areas due to latero-retrusive movement of the mandible even in the cases where any molar contact was not recognized in the articulator. The above results are summarized in TABLE 1. "Laterotrusion Side" means an area that is positioned at the right exterior side and ground off and "Mediotrusion Side" means an inner area of the molars at the left side, when a jaw moves rightward.

TABLE 1

Comparison of grinding patterns evaluated on the Articulator and BruxChecker in no-TMJ symptoms and TMJ symptomatic subjects

| | Normal Subject (N = 36) | | TMJ Symptomatic Subject (N = 14) | |
| --- | --- | --- | --- | --- |
| | Articulator | BruxChecker | Articulator | BruxChecker |
| Laterotrusion Side | | | | |
| Incisor-Canine | 16 (44.4) | 11 (30.6) | 2 (14.3) | 0 |
| Incisor-Canine-Premolar | 9 (25.0) | 14 (38.9) | 5 (35.7) | 2 (14.3) |
| Incisor-Premolar- | 10 (27.8) | 11 (30.6) | 7 (50.0) | 12 (85.7) |

TABLE 1-continued

Comparison of grinding patterns evaluated on the Articulator and BruxChecker in no-TMJ symptoms and TMJ symptomatic subjects

| | Normal Subject (N = 36) | | TMJ Symptomatic Subject (N = 14) | |
|---|---|---|---|---|
| | Articulator | BruxChecker | Articulator | BruxChecker |
| Molar | | | | |
| No-Laterotrusion Contact Mediotrusion Side | 1 (0.03) | 0 | 0 | 0 |
| Mediotrusion Contact* | 21 (58.3) | 13 (36.1) | 13 (92.9) | 1 (7.1) |
| Mediotrusion Grinding** | 2 (0.06) | 23 (63.9) | 1 (7.1) | 13 (92.9) |
| No-Laterotrusion Contact | 13 (36.1) | 0 | 0 | 0 |

Figure 4:
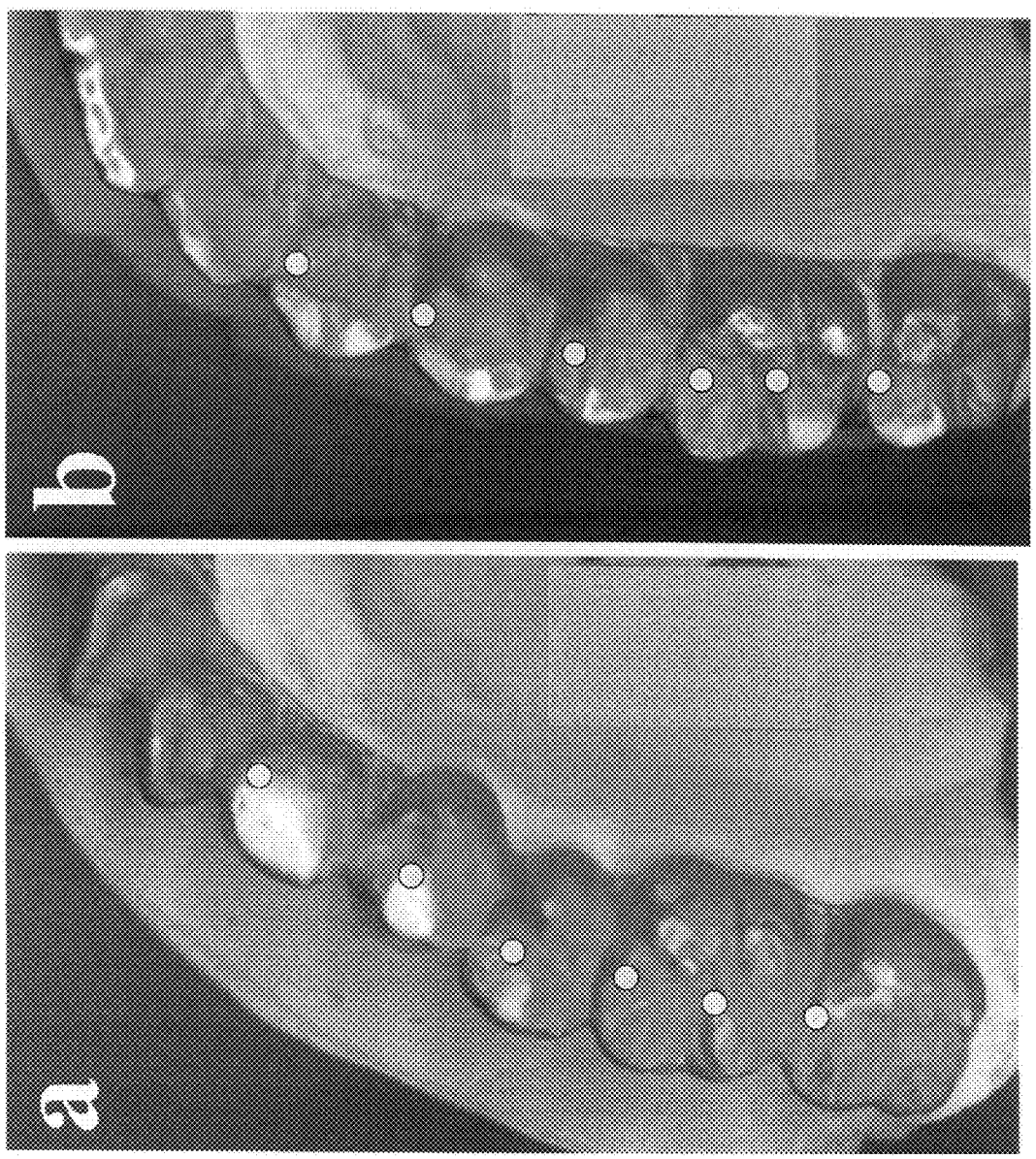
FIGS. 4(a)-(b) are photographs showing the grinding patterns extending laterally and posteriorly. There are observed one type (a) beginning from intercuspal position and the other type (b) not beginning from it depending on a positional relationship from the intercuspation.
Figure 5:
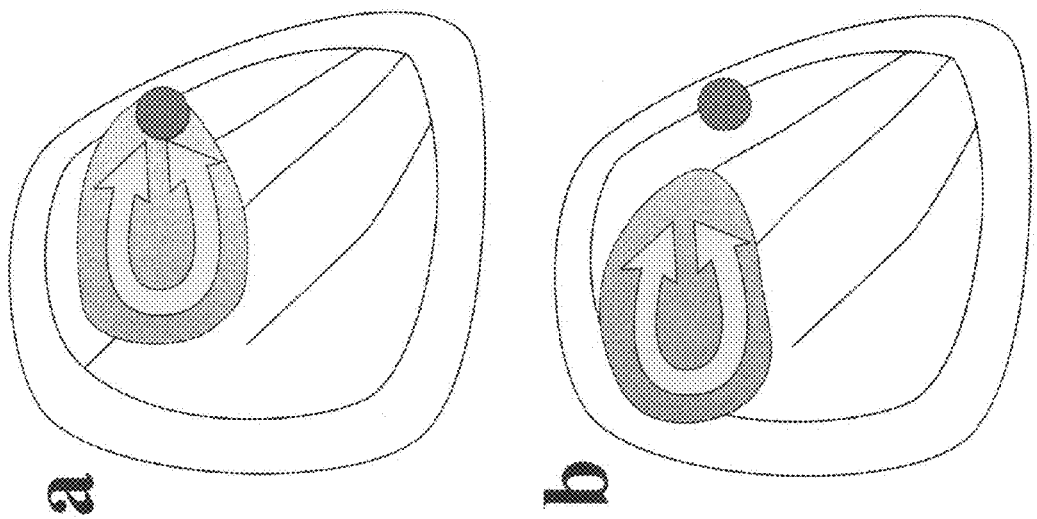
FIGS. 5(a)-(b) show the grinding patterns during the sleep bruxism. There are observed one type (a) beginning from intercuspal position and the other type (b) not beginning from it depending on a positional relationship from the intercuspation.
Figure 6:
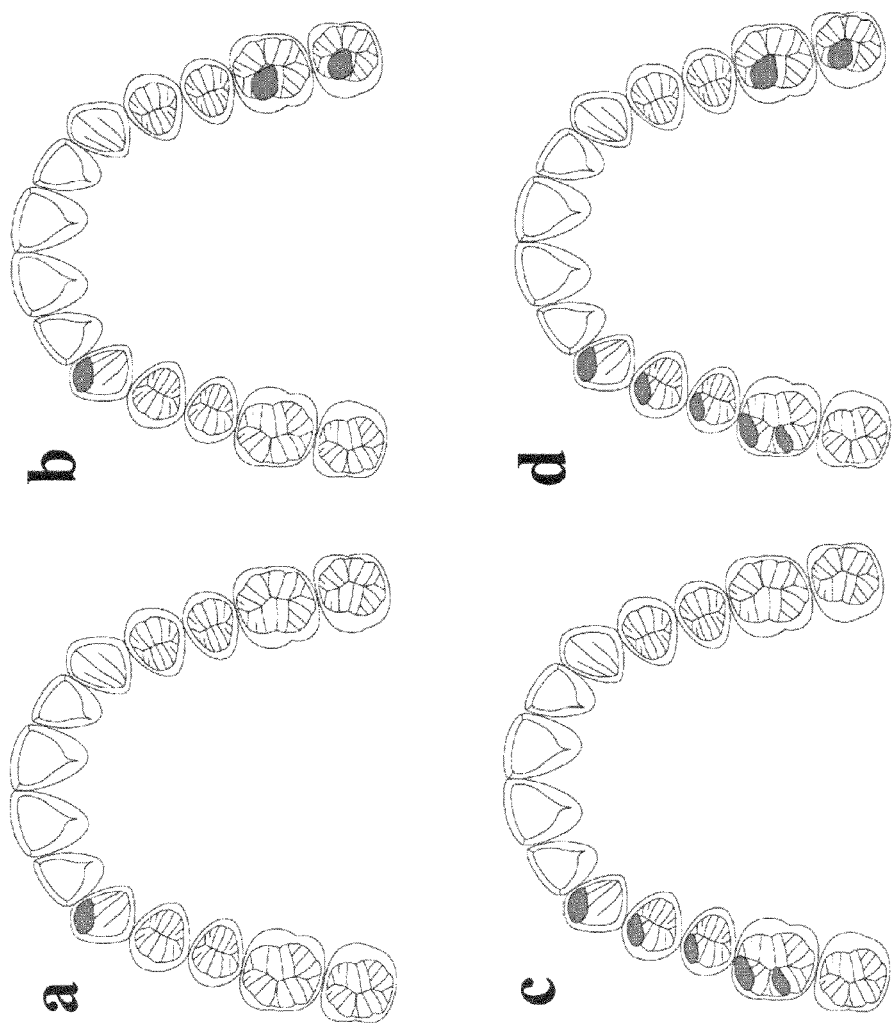
FIGS. 6(a)-(d) schematically show the patterns of the bruxism. Occlusal contact parts during the sleep bruxism are marked with dark color.

*Contact: defined as a cusp contact during mediotrusive movement of the condyle
**Grinding: defined as a wider and expanded facet around the cusp and oblique surface of the cusp than the cusp contact
( ): Percent In most of the cases, the direction of movement during sleep bruxism was latero-retrusive grinding patterns. There were two types: one type (FIG. 4a, FIG. 5a) where the grinding began from intercuspal position (ICP) (the position of a jaw and tooth contacts in occlusion with a maximum occlusal force), and the other type (FIG. 4b, FIG. 5b) where the grinding did not begin from it depending on a positional relationship with the intercuspation. The bruxism patterns obtained in the above Test Example are schematically shown in FIG. 6.

The above Test Examples revealed that observation of the interior of oral cavity or by means of the articulator is different from the occlusal contacts during sleep bruxism identified by the convenient bruxism evaluation apparatus according to the present invention.

The dye and shellac used in the present convenient bruxism evaluation apparatus are tasteless and odorless, and the thickness of the bruxism evaluation sheet after being molded is 0.1 mm or less. The hearing investigation from the subjects shows that they hardly felt a sense of discomfort when they wore the apparatus.

Figure 7:
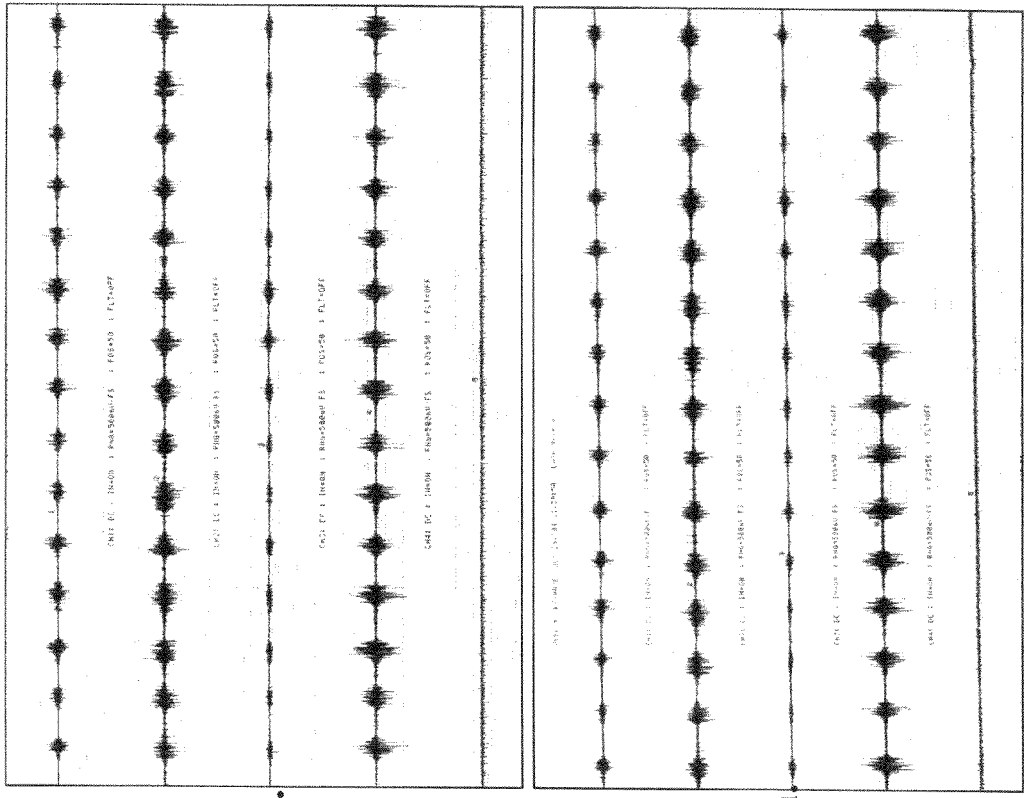
FIG. 7 comprises graphs showing the results obtained with electromyography of masseter and temporalis muscles in the case of mounting of the convenient bruxism evaluation apparatus or not.

Further, electromyography was measured using a polygraph (POLYGRAPH, manufactured by san-ei), with or without the mounting of the convenient bruxism evaluation apparatus, and data were compared with respect to masseter muscles and temporalis muscle. It was then revealed that the activities of these two muscles were almost the same and that there was no significant difference between the activities of these muscles with and without the apparatus, confirming that the mounting of the convenient bruxism evaluation apparatus would not have any effect (FIG. 7).

INDUSTRIAL APPLICABILITY

The present apparatus has made it possible to know occlusal contact position, grinding orientation, contact pattern of whole dentition; and relationship between contact conditions and tooth migration, gingival recession, hyperesthesia and wedge-shaped defect. The apparatus is therefore useful in diagnosis and planning of treatment of occlusion.

The invention claimed is:

1. A bruxism evaluation sheet having a layer comprising an aqueous solution composition of an organic solvent comprising a dye and a thermosetting resin on a base sheet made of a thermoplastic resin.

2. The bruxism evaluation sheet according to claim 1, wherein the thermosetting resin is natural resin.

3. The bruxism evaluation sheet according to claim 2, wherein the natural resin is shellac.

4. The bruxism evaluation sheet according to claim 1, wherein the dye is a food coloring agent.

5. The bruxism evaluation sheet according to claim 4, wherein the food coloring agent is Food Red No. 3.

6. The bruxism evaluation sheet according to claim 4 which comprises 2-2.5% by weight of the dye.

7. The bruxism evaluation sheet according to claim 1, wherein the thermoplastic resin is polyvinyl chloride.

8. The bruxism evaluation sheet according to claim 7, wherein the thickness of the base sheet is in a range of 0.05-0.1 mm.

9. The bruxism evaluation sheet according to claim 2, wherein the dye is a food coloring agent.

10. The bruxism evaluation sheet according to claim 3, wherein the dye is a food coloring agent.

11. The bruxism evaluation sheet according to claim 5, wherein the aqueous solution composition comprises 2-2.5% by weight of the dye.

12. The bruxism evaluation sheet according to claim 1, wherein the organic solvent is an alcohol.

13. The bruxism evaluation sheet according to claim 12, wherein the alcohol is ethanol.

14. The bruxism evaluation sheet according to claim 2, wherein the organic solvent is an alcohol.

15. The bruxism evaluation sheet according to claim 14, wherein the alcohol is ethanol.

* * * * *